United States Patent [19]

Nettleton, Jr. et al.

[11] 4,123,608

[45] Oct. 31, 1978

[54] ANTIBIOTIC COMPOUND

[75] Inventors: Donald E. Nettleton, Jr., Jordan; Terrence W. Doyle, Fayetteville; William T. Bradner, Manlius, all of N.Y.

[73] Assignee: Bristol-Myers Company, New York, N.Y.

[21] Appl. No.: 872,291

[22] Filed: Jan. 25, 1978

Related U.S. Application Data

[63] Continuation-in-part of Ser. No. 816,427, Jul. 18, 1977, abandoned.

[51] Int. Cl.$^2$ ............................................. C07G 11/00
[52] U.S. Cl. .......................................... 536/17; 195/81
[58] Field of Search ....................................... 536/17 A

[56] References Cited

U.S. PATENT DOCUMENTS 4,039,736  8/1977  Nettleton et al. ...................... 536/17

OTHER PUBLICATIONS

Gottlieb et al., Antibiotics.
Fleck et al., Antimicrobial Agents & Chemotherapy, May 1972, pp. 385–391, copyright 1972, American Soc. for Microbiology.

Primary Examiner—Ethel G. Love
Attorney, Agent, or Firm—David M. Morse

[57] ABSTRACT

A novel anthracycline antibiotic designated rudolphomycin is produced by fermentation of *Actinosporangium sp.* ATCC 31127 and isolation of the new antibiotic free of substances co-produced therewith. Rudolphomycin and its pharmaceutically acceptable salts exhibit antimicrobial activity and inhibit the growth of mammalian tumors.

1 Claim, 4 Drawing Figures

FIG. 1

INFRARED ABSORPTION SPECTRUM OF RUDOLPHOMYCIN IN KBr

FIG. 2
ULTRAVIOLET ABSORPTION SPECTRUM OF RUDOLPHOMYCIN IN METHANOL

FIG. 3
PMR SPECTRUM OF RUDOLPHOMYCIN
(100 MHz IN CDCl$_3$, INTERNAL REFERENCE: TMS)

FIG. 4

13CMR SPECTRUM OF RUDOLPHOMYCIN
(25 MHz IN CDCl$_3$, INTERNAL REFERENCE: TMS)

ANTIBIOTIC COMPOUND

CROSS-REFERENCE TO RELATED APPLICATION

This is a continuation-in-part of co-pending application Ser. No. 816,427 filed July 18, 1977, now abandoned.

BACKGROUND OF THE INVENTION (1) Field of the Invention

This invention relates to a new anthracycline antibiotic, to a method for its manufacture, to pharmaceutical compositions containing it and to methods of using said antibiotic as an antimicrobial and antitumor agent.

(2) Description of the Prior Art

There is disclosed in U.S. Pat. No. 4,039,736 the fermentation of *Actinosporangium sp.* ATCC 31127 to produce an antibiotic complex designated therein as bohemic acid complex and the separation of said complex into two novel anthracycline antibiotics designated musettamycin and marcellomycin. Musettamycin and marcellomycin contain the aglycone, ε-pyrromycinone, and have the structural formulae Musettamycin and Marcellomycin By the present invention there has been discovered and isolated in substantially pure form a novel anthracycline antibiotic designated as rudolphomycin. Rudolphomycin has been found by the present inventors to be a minor bioactive component of the bohemic acid complex produced in the fermentation of *Actinosporangium sp.* ATCC 31127.

A number of ε-pyrromycinone glycosides have been described in the literature. Illustrative of such anthracyclines are the following:

1. Cinerubin A and cinerubin B are disclosed in U.K Pat. No. 846,130 [see also U.S. Pat. No. 3,864,480 and Keller-Schierlein et al., *Antimicrobial Agents and Chemotherapy*, page 68 (1970) and Chemical Abstracts, 54, 1466i (1960)].
2. Pyrromycin, an anthracycline antibiotic containing rhodosamine as the glycosidic sugar, is disclosed in Chem. Ber., 92, 1904–1909 (1959).
3. Galirubin A is disclosed in Chemical Abstracts, 64, 3896g (1966) and Chemical Abstracts, 67, 90573z (1967).
4. Rutilantin is described in Biochem. J., 81, 101–104 (1961).

Trypanomycin is described in *Antimicrobial Agents and Chemotherapy*, 1, 385–391 (1972) as having strong antiprotozoal activity. It has an aglycone similar to but not identical with ε-pyrromycinone.

The textbook *Antibiotics*, Volume 1, Mechanism of Action, edited by David Gottlieb and Paul D. Shaw, Springer-Verlag New York, Inc., N.Y., N.Y. (1967) at pages 190–210 contains a review by A. DiMarco entitled Daunomycin and Related Antibiotics.

Information Bulletin, No. 10, International Center of Information of Antibiotics, in collaboration with WHO, December, 1972, Belgium, reviews anthracyclines and their derivatives.

SUMMARY OF THE INVENTION

This invention relates to a novel anthracycline antibiotic designated rudolphomycin and to a process for its preparation and isolation in a purified state free of co-produced substances. The antibiotic is obtained by cultivating a rudolphomycin-producing strain of *Actinosporangium sp.* having the identifying characteristics of ATCC 31127 or a mutant thereof in an aqueous medium containing assimilable sources of carbon and nitrogen under submerged aerobic conditions until a substantial amount of bohemic acid complex is produced by said organism in said culture medium, recovering the bohemic acid complex from the culture medium, separating and isolating the fraction of said complex containing rudolphomycin in admixture with marcellomycin as by chromatography on an alkylated cross-linked dextran adsorbent and separating and isolating rudolphomycin from said mixture free of co-produced substances as by chromatography on silica gel. Rudolphomycin and its pharmaceutically acceptable salts exhibit both antimicrobial and antitumor activity.

DETAILED DESCRIPTION

As mentioned above, rudolphomycin has been found by the present inventors to be a minor component of the bohemic acid complex disclosed in U.S. Pat. No.

4,039,736. That patent describes the fermentation of *Actinosporangium sp.* C-36,145 to produce bohemic acid complex and the separation of said complex into two bioactive components named musettamycin and marcellomycin. There is no disclosure in the patent, however, of the anthracycline antibiotic, rudolphomycin, which has now been found to be co-produced in the fermentation of *Actinosporangium sp.* strain C-36,145.

The above-named bohemic acid-producing organism was obtained from a soil sample taken from Ontario, Canada. A culture of the organism has been deposited without restriction as to availability in the American Type culture Collection, Washington, D.C., and assigned the accession number of ATCC 31127.

The new antibiotic of the present invention has been isolated from bohemic acid complex in an essentially pure form and has been characterized by its physical, chemical and biological properties as described in more detail below.

Properties of Rudolphomycin

Rudolphomycin is an anthracycline antibiotic composed of the aglycone, ε-pyrromycinone, and three glycosidic sugar units, i.e. L-rhodosamine, 2-deoxy-L-fucose and a sugar having the structure From spectral and chemical analysis, rudolphomycin has been determined to have the structure Rudolphomycin in a red solid having a melting point of 171°–175° C. (with decomposition). It is composed of the elements carbon, hydrogen, nitrogen and oxygen in substantially the following average percentages by weight.

Carbon — 58.08
Hydrogen — 6.31
Nitrogen — 3.05
Oxygen (by difference) — 32.56

The calculated molecular formula is $C_{42}H_{52}N_2O_{16} \cdot 1.5\ H_2O$ (The compound is recovered in hydrated form with from 1–2 molecules of water per molecule of anthracycline.).

Figure 1:
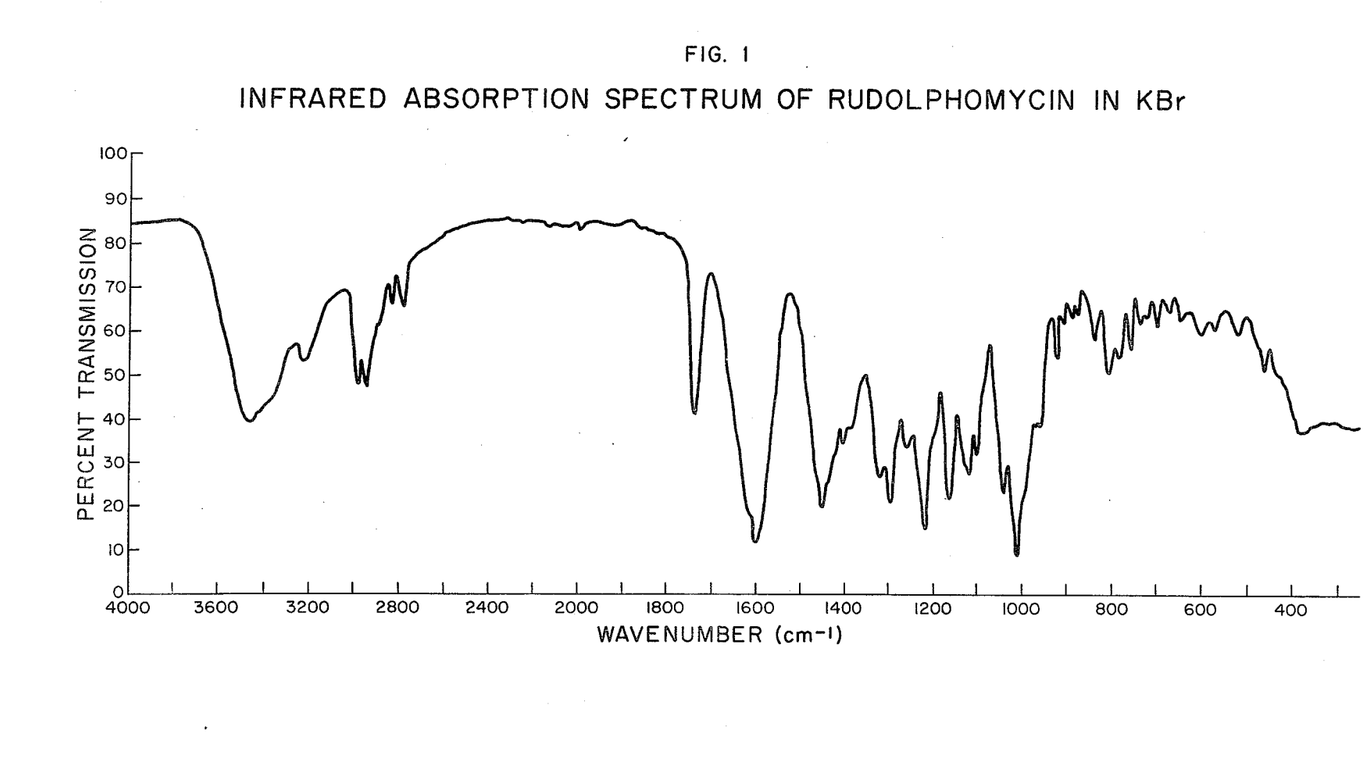
FIG. 1 shows the infrared absorption spectrum of rudolphomycin when pelleted in potassium bromide.

The infrared absorption spectrum of rudolphomycin when pelleted in KBr (1 mg./90 mg. KBr) is shown in FIG. 1 of the accompanying drawings. Characteristic infrared absorption bands are exhibited at the following frequencies expressed in reciprocal centimeters: 3460, 3410, 2980, 2940, 2820, 2770, 1735, 1600, 1450, 1315, 1295, 1220, 1160, 1118, 1040, and 1010.

Figure 2:
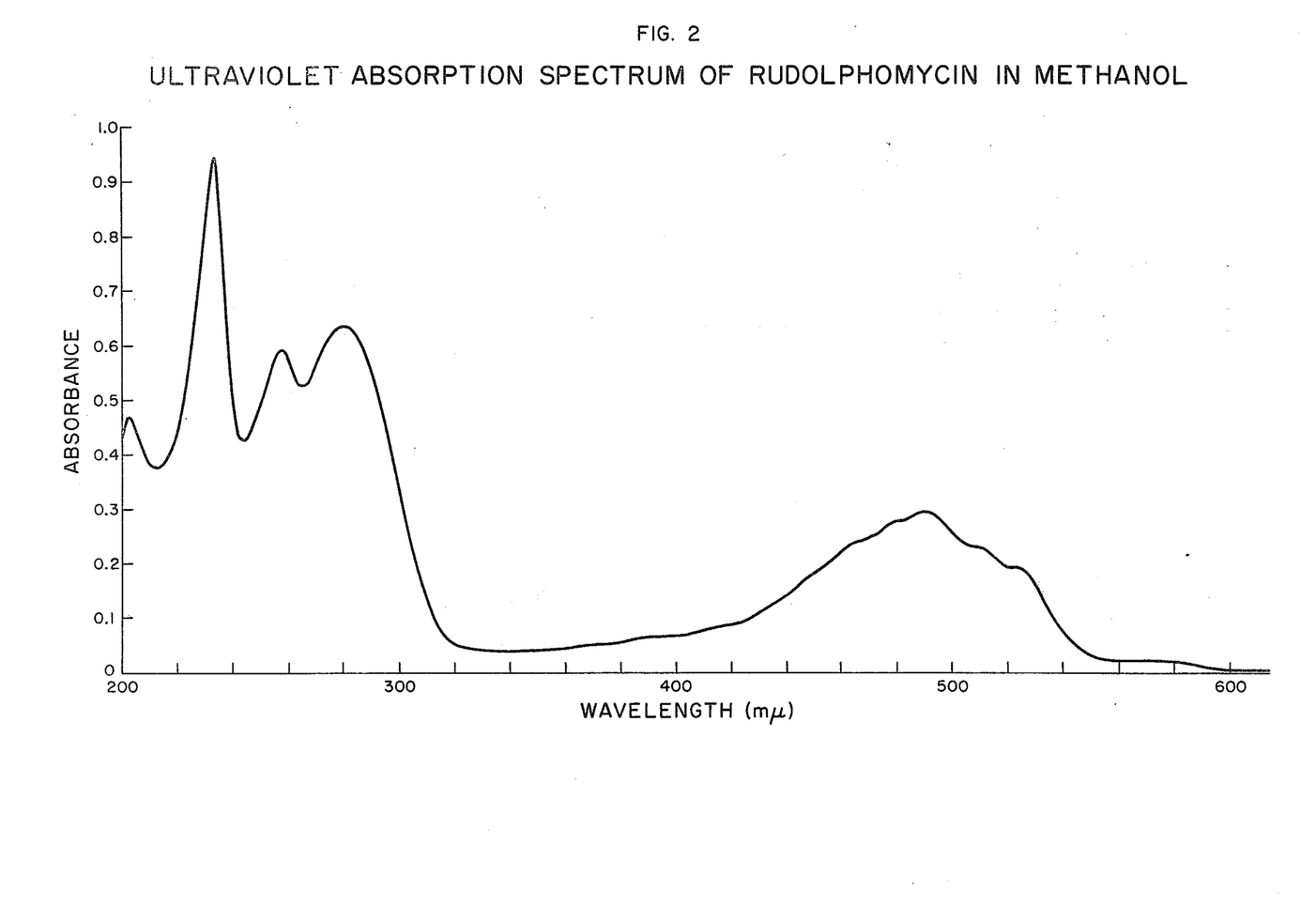
FIG. 2 shows the ultraviolet absorption spectrum of rudolphomycin in methanol.

The ultraviolet absorption spectrum of rudolphomycin in methanol (0.01795 g./l.) is shown in FIG. 2 of the drawings. Observed absorption maxima and absorptivities are as follows: 233 mμ, 53.01; 257 mμ, 33.2; 280 mμ, 35.43; 490 mμ, 16.46; shoulders at 466, 480, 511 and 523 mμ.

A proton magnetic resonance spectrum of rudolphomycin was determined with a Varian HA-100 spectrometer operating at 100 MHz by dissolving about 28 mg. of the antibiotic in 0.5 ml. of $CDCl_3$ and using tetramethylsilane (TMS) as the internal reference. Observed chemical shifts (in ppm) and the pattern description were as follows: 7.68 (s, 1H, $C_{11}$-H), 7.28 (s, 2H, $C_2$-H + $C_3$H), 5.53 (bs, 1H), 5.32 (s, 1H), 5.28 (m, 1H), 5.26 (s, 1H), 5.10 (m, 2H, 1 exchangeable) (area from 5.53-5.0 assigned to $C_7$-H + anomeric protons + possible olefinic proton), 4.56 (m, 3H), 4.14 (s, 1H, $C_{10}$-H), 4.10 (m, 4H), 3.80 (m, 2H), 3.72 (s, 3H, $CO_2CH_3$), 2.20 (s, 6H, $N(CH_3)_2$, 2.70 to 1.60 (m, 12H), 1.28 (m, ~12H, doublets and triplet for 4$CH_3$ groups).

A proton magnetic resonance spectrum of rudolphomycin was also determined with a Varian XL-100 spectrometer operating at 100 MHz dissolving 15 mg. of the antibiotic in 0.5 ml. of deuterated pyridine ($C_5D_5N$) and using tetramethylsilane (TMS) as the internal reference. Observed chemical shifts (in ppm) and pattern descriptions were as follows: 7.88 (s, 1H, $C_{11}$-H), 7.39 (s, 2H, $C_2$, $C_3$-H's), 5.88 (s, 1H), 5.82 (bs, 1H), 5.71 (s, 1H), 5.52 (Q, 1H, coupled to $CH_3$ at 1.71), 5.45 (m, 1H, coupled to $CH_2$ or CH in 2.5-3.0 region), 5.29 (bs, 1H), 4.84 (m, 1H, coupled to $CH_3$ at 1.54), 4.74 (m, 1H, coupled to $CH_2$ or CH in 2.5-3.0 region), 4.48 (s, 1H, $C_{10}$-H), 4.37 (m, 1H, coupled to $CH_3$ at 1.45), 4.23 (bs, 1H), 3.93 (bs, 1H, coupled to $CH_2$ or CH in 2.0-2.5 area), 3.72 (s, 3H, $CO_2CH_3$), 2.5-3.0 (m, 3H, 2.0-2.5 (m), 2.13 (s, 6H, $N(CH_3)_2$), 1.71 (d, 3H, $CH_3$-coupled to CH at 5.52), 1.54 (d, 3H, $CH_3$-coupled to CH at 4.84), 1.45 (d, 3H, $CH_3$ coupled to CH at 4.37), 1.39 (t, 3H, $C_{14}$ protons).

Figure 3:
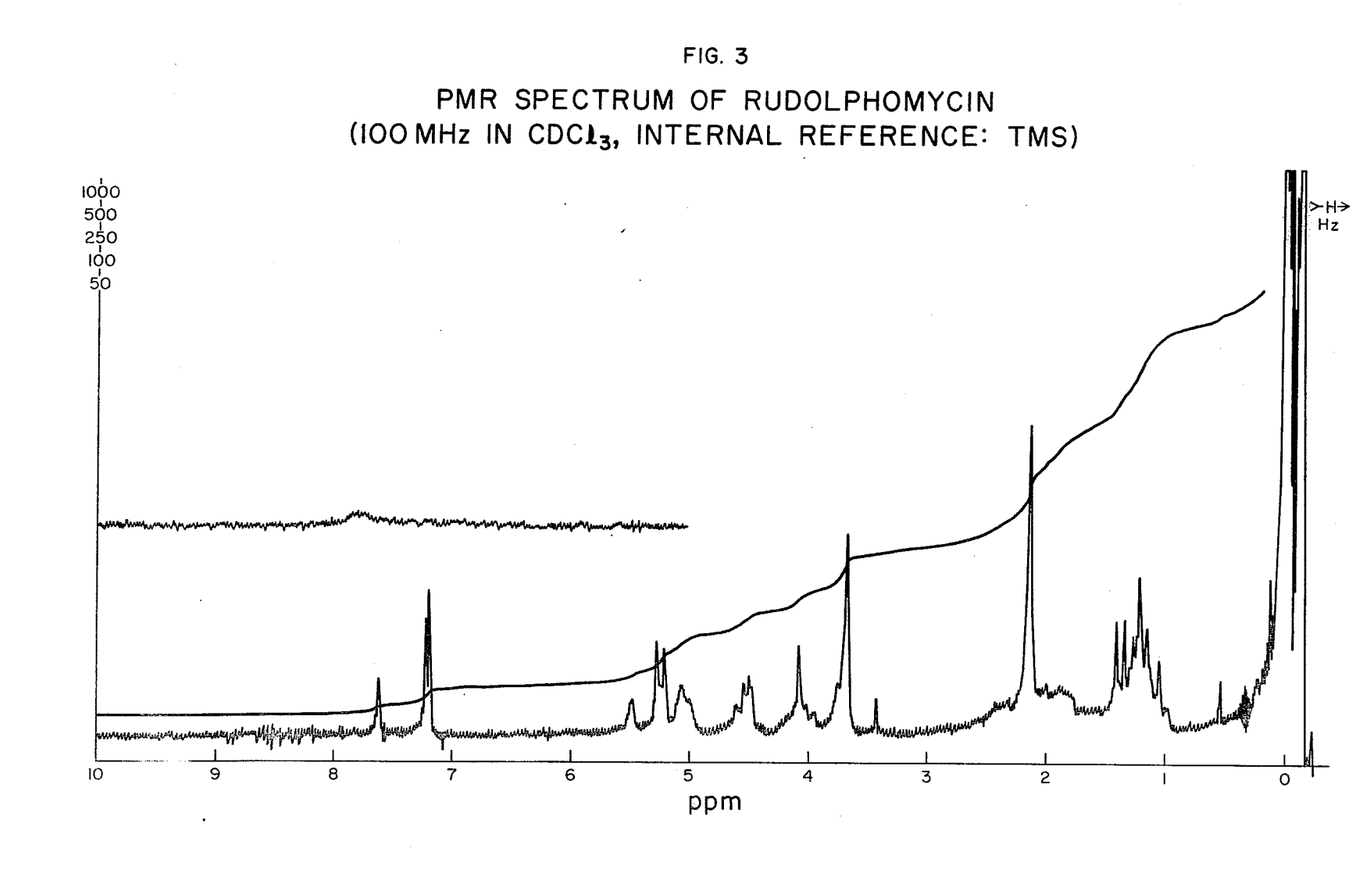
FIG. 3 shows the proton magnetic resonance spectrum of rudolphomycin in CDCl$_3$ (100 MHz).
Figure 4:
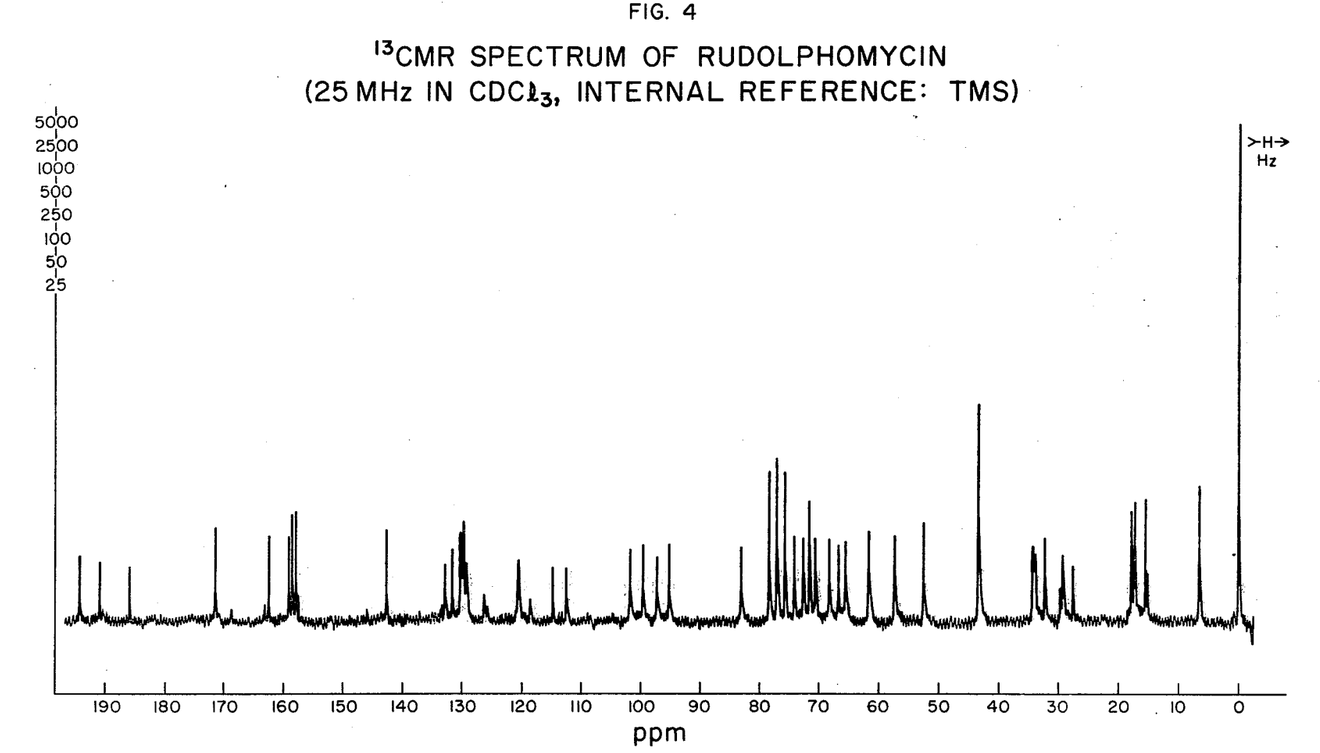
FIG. 4 shows the carbon-13 magnetic resonance spectrum of rudolphomycin in CDCl$_3$ (25 MHz).

A carbon-13 nuclear magnetic resonance spectrum of rudolphomycin was determined with a Varian XL-100 spectrometer operating at 25 MHz by dissolving about 70 mg. of the antibiotic in 0.5 ml. of $CDCl_3$ and using tetramethylsilane (TMS) as the internal reference. The resonance spectrum is shown in FIG. 3 of the drawings. Observed chemical shifts (in ppm relative to tetramethylsilane) and multiplicities for $^{13}C$ magnetic resonance spectra of rudolphomycin in $CDCl_3$, $CD_2Cl_2$ and DMSO-$d_6$ solvents are as follows:

| | | Rudolphomycin[13] CMR Listings | | | |
|---|---|---|---|---|---|
| | | PPM | | Multiplicity | |
| No. | $CDCl_3$ | $CD_2Cl_2$ | $DMSO-d_6$ | $DMSO-d_6$ | Assignments |
| 1 | 194.1 | 193.7 | 192.7 | s | $C_4'''$ |
| 2 | 190.6 | 190.8 | 188.5 | s | $C_5$ |
| 3 | 185.6 | 185.0 | 184.1 | s | $C_{12}$ |
| 4 | 171.2 | 171.3 | 170.4 | s | $C_{15}$ |
| 5 | 162.3 | 162.4 | 161.2 | s | $C_6$ |
| 6 | 159.0 | 158.8 | 161.2 | s | ⎫ |
| 7 | 158.5 | 158.6 | 157.0 | s | ⎬ $C_1, C_4, C_2'''$ |
| 8 | 157.8 | 158.0 | 156.5 | s | ⎭ |
| 9 | 142.6 | 142.9 | 141.8 | s | $C_{10a}$ |
| 10 | 132.8 | 132.9 | 131.3 | s | ⎫ |
| | | | | | ⎬ $C_{6a}, C_{11a}$ |
| 11 | 131.6 | 131.5 | 131.1 | s | ⎭ |
| 12 | 130.1 | 130.2 | 129.5 | d | ⎫ |
| | | | | | ⎬ $C_2, C_3$ |
| 13 | 129.6 | 130.0 | 128.8 | d | ⎭ |
| 14 | 120.4 | 120.5 | 118.7 | d | $C_{11}$ |
| 15 | 114.8 | 114.8 | 113.6 | s | $C_{5a}$ |
| 16 | 112.5 | 112.5 | 111.3 | s | $C_{12a}$ |
| 17 | 112.4 | 112.4 | 111.1 | s | $C_{4a}$ |
| 18 | 101.6 | 101.9 | 100.4 | d | |
| 19 | 99.5 | 99.6 | 98.3 | d | ⎫ $C_1', C_1'', C_1''',$ |
| 20 | 97.1 | 96.9 | 95.6 | d | ⎬ $C_3''''$ |
| 21 | 95.1 | 95.8 | 92.9 | d | |
| 22 | 83.1 | 83.8 | 80.0 | d | ⎭ |
| 23 | 74.3 | 74.4 | 73.3 | d | |
| 24 | 72.6 | 72.3 | 70.0 | s | $C_9$ |
| 25 | 71.7 | 71.8 | 69.9 | d | |
| 26 | 70.7 | 70.9 | 68.9 | d | |
| 27 | 68.4 | 68.6 | 67.4 | t or d | |
| 28 | 66.8 | 67.0 | 66.5 | d | |
| 29 | 65.6 | 65.8 | 64.6 | d | |
| 30 | 61.7 | 62.0 | 61.1 | d | |
| 31 | 57.3 | 57.6 | 56.4 | d | |
| 32 | 52.4 | 52.6 | 52.2 | Q | $C_{16}$ |
| 33 | 43.2 | 43.4 | 42.9 | Q | $(N(CH_3)_2$ |
| 34 | 34.3 | 34.6 | 33.6 | t | |
| 35 | 34.1 | 34.3 | 33.3 | t | ⎬ $C_2, C_8, C_2''$ |
| 36 | 32.3 | 32.6 | 31.4 | t | |
| 37 | 29.3 | 29.6 | 28.9 | t | $C_{13}$ |
| 38 | 17.9 | 18.0 | 17.4 | Q | |
| 39 | 17.4 | 17.6 | 17.1 | Q | ⎬ $C_6', C_6'', C_6'''$ |
| 40 | 15.7 | 15.9 | 16.2 | Q | |
| 41 | 6.7 | 6.9 | 6.6 | Q | $C_{14}$ |

In a solvent system consisting of toluene:methanol:acetone (3:1:1) (v/v), rudolphomycin exhibits an $R_f$ value of 0.31–0.34 as determined by silica gel thin layer chromatography.

When subjected to high pressure liquid chromatography under the following conditions, rudolphomycin has a retention time of 5.0 minutes.

Instrument: Waters Associates, Inc. modular components
Column: 30 cm. × 4 mm. μ-PORASIL column
Mobile Phase: $CH_2Cl_2:CH_3OH:NH_4OH$ (conc.) in a ratio of 96:4:1
Flow Rate: 1.5 ml./min.
Detector: 254 mμ UV detector (Varian Associates, Inc.)

A sample of rudolphomycin was subjected to field desorption mass spectrometry (fdms). The compound gave a parent ion (molecular ion + 1) at 841 and in addition ions at 716 and 586. Inasmuch as fdms usually shows molecular ions + 1 mass unit, the data corresponds to molecular ions of 840, 715 and 585. The molecular weight of rudolphomycin thus calculates as 840.

Rudolphomycin forms salts with both acids and bases and pharmaceutically acceptable salts with such acids and bases are included within the scope of the present invention. Examples of such pharmaceutically acceptable salts will be obvious to those skilled in the art from knowledge of other anthracycline antibiotics of this type. The salts are readily obtained by reacting rudolphomycin in an inert solvent with the appropriate acid or base. Illustrative of such pharmaceutically acceptable salts are salts with organic or inorganic acids such as hydrochloric, hydrobromic, sulfuric, nitric, phosphoric, acetic or propionic, salts with metallic cations such as the alkali metal or alkaline earth metal cations, e.g. sodium, potassium, calcium or magnesium, and ammonium or organic amine salts such as ethanolamine, ethylenediamine, diethanolamine, procaine or triethanolamine.

Preparation of the novel anthracycline antibiotic of the present invention is described below.

The Microorganism

The strain C-36,145 has the following morphological characteristics. The strain forms a sporangium-like body (false sporangium) on the tip of the sporophore, which is an agglomeration of a thickly coiled spore-chain. The spore-chain often interlaces with the neighboring aerial hyphae, and it develops to the sporangium-like structure covered by a viscid material. The sporangium-like body and aerial mycelium are formed on glucose-asparagine agar, tyrosine agar, yeast extract-malt extract agar and oat meal agar. In addition to the formation of a large number of false sporangia, there are also produced ordinary spore-chains, though much less in number, which form open spirals. Spores in the sporangium-like body are smooth in surface, ellipsoidal in shape and non-motile. Spores in the ordinary spore-chain are of oval shape and have a smooth or occasionally warty surface. Primary mycelium is branched, non-septated and non-fragmented.

Table 1 reports the cultural properties obtained on various media. Strain C-36,145 grows well on most of the agar media tested, but the formation of aerial mycelium and the sporulation are somewhat slow. Mass color of the aerial mycelium is light greenish gray. Reverse side of the growth is reddish orange to red in glucose-asparagine agar, inorganic salts-starch agar, yeast extract-malt extract agar and oat meal agar. It produces melanoid pigment in tyrosine agar and peptone-yeast extract-iron agar.

The physiological characteristics and carbohydrate utilization of strain C-36,145 are shown in Tables 2 and 3, respectively. The growth temperature ranged from 20° to 37° C. and no proliferation was seen at 43° C.

Strain C-36,145 contains LL-diaminopimelic acid (LL-DAP) and glycine as characteristic amino acid components in the cell wall. Diagnostic carbohydrate was not present.

The morphological, cultural and physiological characteristics of Strain C-36,145 are similar to those of the genus Streptomyces except for the formation of sporangium-like body. The cell wall composition is also similar to that of the type I group (*Streptomyces* type) according to the classification of Lechevalier and Lechevalier in Int. J. Syst. Bacteriol. 20:435-443 (1970). The sporangium-like body of strain C-36,145 appears to be different from the normal sporangium produced by the well-defined sporangium-forming genera in that (1) the latter form small sporangia at an early stage of the growth which mature with time and (2) ordinary sporangia are usually not covered by a viscous material.

Krassilnikov and Tsi-Shen proposed in 1961 a new genus of *Actinosporangium* in the family *Actinoplanaceae* (later transferred to the family *Streptosporangiaceae*) for the organism producing a spore mass which was very similar to sporangium (Isv. Akad. Navk. USSR, Ser. Biol., 113–116, 1961). Subsequently, the sporangium-like body was found to be a viscid spore-forming mass and different from the real sporangium, and the genus *Actinosporangium was placed in the family Streptomycetaceae* on the basis of its morphological characteristics and the cell wall composition of the type I group.

Thus, on the basis of all the available data, Strain C-36,145 is considered to be a new species of the genus *Actinosporangium*. It should be noted, however, that only two species in the genus *Actinosporangium* have been reported in the literature and hence the genus has not yet been fully established (see H. Prauser: The Actinomycetales. The Jena Intl. Sym. on Taxonomy. Sept., pp. 329–335, 1968. Veb. Gustav Fischer Verlag, JENA, 1970).

It is to be understood that the present invention is not limited to use of the particular Strain C-36,145 or to organisms fully answering the above descriptions. It is especially intended to include other rudolfomycin-producing strains or mutants of the said organism which can be produced from the described organism by various means including x-radiation, ultraviolet radiation, treatment with nitrogen mustards, phage exposure, and the like.

Table 1

| | Cultural Characteristics of Strain C-36,145 | | | |
|---|---|---|---|---|
| | Growth | Reverse Color | Aerial Mycelium | Diffusible pigment |
| Sucrose-nitrate agar | Moderate | Yellowish pink | Scant, whitish | None |
| Glucose-asparagine agar | Good | Reddish orange to red | Abundant, greyish leaf | None or reddish orange |
| Glycerol-asparagine agar | Good | Rose | Moderate, light grey to pale pink | None or reddish pink |
| Inorganic salts-starch agar | Moderate | Reddish orange to deep red | Poor, greyish leaf | Light orange, partially light yellow |
| Tyrosine agar | Good | Brown to deep purplish-brown | Poor, greyish leaf | Dark brown |
| Nutrient agar | Poor | Colorless | None | None |
| Yeast extract-malt extract agar | Good | Deep red greyish pink | Moderate, greyish leaf partially | Light brown |
| Oat meal agar | Moderate | Vivid reddish orange | Moderate, greyish leaf | Vivid orange |
| Peptone-yeast extract-iron agar | Moderate | Black | None | Black |

Table 2

| | Physiological Characteristics of Strain C-36,145 | |
|---|---|---|
| Tests | Responses | Methods and Materials Employed |
| Nitrate reduction in inorganic medium | Strongly positive | Czapek's sucrose nitrate broth |
| Nitrate reduction in organic medium | Strongly positive | Nitrate medium, consisted of yeast yeast extract 0.5%, glucose 1.0%, KNO₃ 0.5% and CaCO₃ 0.1%. |
| Skim-milk agar | Abundant growth, Negative hydrolysis. Deep yellowish-red to deep reddish-purple mycelial pigment. | Leudeman's medium [Intl. J. Syst. Bacteriol. 21-240-247 (1971)] |
| 10% Skim-milk solution | Brownish broth color. Reddish-orange ring growth. No peptonization nor coagulation. | |
| Gelatin slab | Rapid and complete liquefaction. | Basal medium: Yeast extract 0.4% malt extract 1.0% and glucose 0.4%. |
| Melanin formation | Strongly positive | Tyrosine agar and peptone-yeast extract-iron agar. |
| Growth-temperature | Optimal growth at 28° C. Moderate growth at 20-37° C. Slow growth at at 15° C. No growth at 10° C. and 43° C. | Yeast extract-malt extract agar. |

Table 2-continued

| Tests | Physiological Characteristics of Strain C-36,145 | |
|---|---|---|
| | Responses | Methods and Materials Employed |
| NaCl tolerance | Moderate growth at 0.5–4%-NaCl. No growth at 8%-NaCl. | Basal medium: 1%-yeast extract, 2%-soluble starch and 1.5% agar. |

Table 3

| Carbohydrate Utilization of Strain C-36,145 | |
|---|---|
| D(−)-Arabinose | − |
| L(+)-Arabinose | ++ |
| D-Xylose | ++ |
| D-Ribose | ++ |
| L-Rhamnose | ++ |
| D-Glucose | ++ |
| D(+)-Galactose | ++ |
| D-Fructose | ++ |
| D-Mannose | ++ |
| Sucrose | ++ |
| Maltose | ++ |
| Lactose | ++ |
| D(+)-Melibiose | ++* |
| Raffinose | ++* |
| D(+)-Melezitose | − |
| Soluble starch | ++ |
| Cellulose | − |
| Glycerol | ++ |
| Inositol | ++ |
| D-Mannitol | ++* |
| Sorbitol | − |
| Dulcitol | − |

Basal medium: Pridham-Gottlieb medium
*Rich production of reddish-orange pigment Preparation of Bohemic Acid Complex Bohemic acid complex may be produced by cultivating a bohemic acid-producing strain of Actinosporangium sp. having the characteristics of A.T.C.C. 31127 or a mutant thereof under submerged aerobic conditions in an aqueous nutrient medium. The organism is grown in a nutrient medium containing an assimilable carbon source, for example an assimilable carbohydrate. Examples of suitable carbon sources include sucrose, lactose, maltose, mannose, fructose, glucose, glycerol and soluble starch. The nutrient medium should also contain an assimilable nitrogen source such as fish meal, peptone, soybean flour, peanut meal, cotton seed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of the bohemic acid complex can be effected at any temperature conducive to satisfactory growth of the organism, e.g. 20°-37° C., and is conveniently carried out at a temperature of about 27° C.

The medium normally is slightly alkaline, but the exact pH can be varied widely depending on the particular medium used.

The fermentation may be carried out in Erlenmeyer flasks or in laboratory or industrial fermentors of various capacities. When tank fermentation is to be used, it is desirable to produce a vegetative inoculum in a nutrient broth by inoculating a small volume of the culture medium with the spore form of the organism. After obtaining an active inoculum in this manner, it is transferred aseptically to the fermentation tank medium for large scale production of the antibiotics. The medium used for the vegetative inoculum can be the same as that employed for larger fermentations, although other media can be employed.

As is customary in aerobic submerged culture processes, sterile air is blown through the culture medium.

Agitation may be maintained by means of agitators generally familiar to those in the fermentation industry.

In general, optimum production of the bohemic acid complex is achieved after incubation periods of about 190-210 hours in stir-jar fermentors or tank fermentors. The course of the fermentation can be followed by assaying the fermentation medium from time to time against an organism susceptible to the bohemic acid complex, e.g. D. pneumoniae, St. pyogenes or S. aureus.

The bohemic acid complex may be recovered from the fermentation medium by extraction with a water-immiscible organic solvent, for example chlorinated hydrocarbons (e.g. methylene chloride, chloroform), water-immiscible alcohols (e.g. n-butanol or amyl alcohol), alkyl esters of fatty acids (e.g. ethyl acetate, butyl acetate) or ketones (methyl isobutyl ketone, methyl amyl ketone). Polar organic solvents such as n-butanol, methyl isobutyl ketone or ethyl acetate are most advantageously used with methyl isobutyl ketone being a most preferred extraction solvent. The majority of the antibiotic activity is found in the broth, and thus the broth may be filtered prior to extraction. In the preferred procedure, however, the whole fermentation broth is extracted with the organic solvent at a pH of between about 7.5 and 8.5. The organic phase may then be filtered and dried to give the solid bohemic acid complex. Alternatively, the organic extract may be concentrated and the solid complex precipitated by dilution with a suitable antisolvent such as Skellysolve B (isomeric hexanes).

Since it has been determined that all active components of bohemic acid complex are aminoglycosides capable of forming salts with acids, the crude bohemic acid mixture is preferably freed of some of the inactive components at this stage by dissolving it in a water-immiscible organic solvent, e.g. methylene chloride, and extracting into an aqueous solution, e.g. 0.1N acetic acid. The aqueous phase is separated, neutralized to pH 7 as with NaHCO$_3$ and extracted with a water-immiscible organic solvent such as methylene chloride. Essentially all of the bioactive components are found in this methylene chloride phase with an overall reduction to 25% of the original weight of the crude bohemic acid complex.

Separation and Isolation of Rudolphomycin

The bohemic acid complex as produced by the above fermentation process contains musettamycin and marcellomycin as the principal bioactive components. It has been found according to the present invention, however, that a third bioactive anthracycline, rudolphomycin, is present in the complex as a minor component. This new component may be separated from the complex in a highly purified state free of co-produced substances and shown to be a novel anthracycline antibiotic by its characteristic physical, chemical and biological properties.

A method for separating bohemic acid complex into musettamycin and marcellomycin is described in U.S. Pat. No. 4,039,736. In that procedure a solution of bohemic acid complex in a suitable organic solvent (e.g.

chloroform) is chromatographed on a column packed with a suitable adsorbent such as an alkylated cross-linked dextran (e.g. Sephadex LH-20 available from Pharmacia Fine Chemicals, Inc.). The marcellomycin and musettamycin components are then eluted from the adsorbent with a suitable organic solvent such as chloroform. Multiple fractions are collected and, after suitable dilution, their adsorbancies are monitored by a colorimeter at 490 mμ. The adsorbancies are plotted graphically against the corresponding fraction numbers to determine peaks for the components eluted from the column. The appropriate musettamycin and marcellomycin fractions, as determined from the elution sequence, are combined and evaporated to give the solid individual antibiotics in partially purified form. The solids may then be recrystallized from a suitable organic solvent such as acetonitrile, methanol or chloroform - Skellysolve B.

In carrying out the above chromatographic separation, four distinct bands of anthracycline pigments are noted which may be recovered as partially purified solids. The first two bands to elute comprise inactive fractions. The third band is found to be musettamycin. Band four is predominantly marcellomycin, but thin layer chromatography (6:2:2) (toluene:methanol:acetone) (v/v) indicated a second component having the same $R_f$ as musettamycin (0.31-0.34). At first this had been presumed to be unseparated musettamycin, but careful rechromatography on Sephadex LH-20 failed to produce additional amounts of that antibiotic. Only a single peak eluted, and this by thin layer chromatography was still a mixture having the same composition as the starting material. It has now been found, according to the present invention, that the solids obtained from the fourth band upon LH-20 chromatography of bohemic acid complex comprise a mixture of marcellomycin and a new anthracycline antibiotic which has been given the name of rudolphomycin. Separation and isolation of rudolphomycin from the above-mentioned mixture of rudolphomycin and marcellomycin may be effected by the chromatographic procedure described below.

The solids (rudolphomycin and marcellomycin mixture) obtained from the fourth band upon LH-20 chromatography of bohemic acid complex are dissolved in a suitable organic solvent such as 19:1 toluene:methanol (v/v). This solution is chromatographed on a column packed with acid-washed silica gel which is then developed with a suitable organic solvent such as 19:1 toluene:methanol (v/v). In packing the column the silica gel is suspended in an appropriate solvent system which may conveniently be the same as that used for the developing solvent. Best results are obtained if the silica gel is neutralized prior to development, for example by treatment of the column (silica gel + solvent system) with sufficient concentrated ammonium hydroxide to give a pH reading of about 8. The fractions eluting from the column are monitored either by thin layer chromatography or by a colorimeter (490 mμ) and fractions containing exclusively or nearly exclusively rudolphomycin are evaporated to dryness to give the antibiotic in highly purified form substantially free of marcellomycin and other co-produced substances of the bohemic acid complex.

If desired, rudolphomycin may be further purified by use of the high pressure liquid chromatography procedure described in detail in Example 8. This procedure has been found to give extremely pure samples of the antibiotic.

For production of larger amounts of rudolphomycin, a preparative HPLC system using a silica gel column may be employed. Example 9B provides a detailed description of a preferred system for providing multigram quantities of the purified antibiotic.

Biological Activity Data

The in vitro minimum inhibitory concentrations (MIC) or rudolphomycin were determined for a number of microorganisms using the standard tube dilution procedure. The results of this screening are shown in the table below.

| Antimicrobial Spectrum of Rudolphomycin | |
|---|---|
| Test Organism | MIC in μg./ml. |
| Bacteria: | |
| Streptococcus pneumoniae A-9585 | 0.25 |
| Streptococcus pyogenes A-9604 | 0.5 |
| Staphylococcus aureus A-9537 | 2 |
| Staphylococcus aureus A-9606 | 8 |
| Streptococcus faecalis A-20688 | 4 |
| Escherichia coli A-15119 | >63 |
| Escherichia coli A-20341-1 | >63 |
| Klebsiella pneumoniae A-15130 | >63 |
| Proteus mirabilis A-9900 | >63 |
| Proteus vulgaris A-9716 | >63 |
| Serratia marcescens A-20019 | >63 |
| Enterobacter cloacae A-9659 | >63 |
| Pseudomonas aeruginosa A-9843A | >63 |
| Fungi: | |
| Candida albicans A-9540 | >125 |
| Candida tropicalis A-15051 | >125 |
| Candida krusei A-15052 | >125 |
| Cryptococcus neoformans A-15053 | 63 |
| Trichophyton mentagrophytes A-9870 | >125 |
| Microsporum canis A-9872 | >125 |

The compound of the present invention was also tested against the transplantable mouse tumor L-1210 lymphatic leukemia which is responsive to anthracycline-type antitumor agents. The methodology used generally followed the protocols of the National Cancer Institute (*Cancer Chemotherapy Rep.*, Part 3, 3, 1–103 (1972). The essential experimental details are given at the bottom of the following table. Four different dose regimens were tested: (1) single dose, (2) day 1 + every third day (days 1,4 and 7), (3) daily for 5 days (QD 1→5), and daily for 9 days (QD 1→9). There was little evidence of schedule dependence except that the QD 1→9 treatment may be the least effective.

| | | Effect of Rudolphomycin on L-1210 Leukemia | | | | | |
|---|---|---|---|---|---|---|---|
| Material | Days Treated | Total inj. Schedule | Dose mg./kg./inj. | MST Days | Effect MST % T/C | Average Weight Change, g. | Survivors Day 5 |
| Rudolphomycin | 1 | 1 | 12.8 | 10.0 | 143 | −2.5 | 3/6 |
| | | | 6.4 | 10.0 | 143 | +0.3 | 3/6 |
| | | | 3.2 | 10.0 | 143 | +0.3 | 5/6 |
| | | | 1.6 | 8.0 | 114 | +0.6 | 6/6 |
| | | | 0.8 | 8.0 | 114 | +1.6 | 6/6 |
| | | | 0.4 | 8.0 | 114 | +1.0 | 6/6 |
| Rudolphomycin | 1, 4, 7 | 3 | 6.4 | 9.0 | 129 | −0.6 | 4/6 |
| | | | 3.2 | 7.0 | 100 | −2.4 | 4/6 |

-continued

Effect of Rudolphomycin on L-1210 Leukemia

| Material | Days Treated | Total inj. Schedule | Dose mg./kg./inj. | MST Days | Effect MST % T/C | Average Weight Change, g. | Survivors Days |
|---|---|---|---|---|---|---|---|
| Rudolphomycin | 1→ 5 | 5 | 1.6 | 10.0 | 143 | +0.5 | 6/6 |
| | | | 0.8 | 9.5 | 136 | +1.2 | 6/6 |
| | | | 0.4 | 8.0 | 114 | +2.7 | 6/6 |
| | | | 0.2 | 8.0 | 114 | +1.7 | 6/6 |
| | | | 3.2 | 9.0 | 129 | −0.6 | 4/6 |
| | | | 1.6 | 9.0 | 129 | −0.4 | 5/6 |
| | | | 0.8 | 10.0 | 143 | +0.3 | 6/6 |
| | | | 0.4 | 9.0 | 129 | +0.9 | 6/6 |
| | | | 0.2 | 9.0 | 129 | +2.2 | 6/6 |
| | | | 0.1 | 8.0 | 114 | +0.8 | 6/6 |
| Rudolphomycin | 1→ 9 | 9 | 1.6 | 7.5 | 107 | −0.9 | 6/6 |
| | | | 0.8 | 9.0 | 129 | +0.2 | 6/6 |
| | | | 0.4 | 9.0 | 129 | +1.0 | 6/6 |
| | | | 0.2 | 9.0 | 129 | +1.0 | 6/6 |
| | | | 0.1 | 7.5 | 107 | +2.9 | 6/6 |
| | | | 0.05 | 8.0 | 114 | +3.0 | 6/6 |
| Control | Saline | | — | 7.0 | — | +3.1 | 10/10 |

Tumor inoculum: $10^6$ ascites cells implanted i.p.
Host: BDF$_1$ ♀ mice
Evaluation: MST = median survival time
Effect: % T/C = MST treated/MST control × 100
Criteria: T/C ≧ 125 considered significant antitumor effect.

As indicated by the antimicrobial and mouse tumor data provided above, rudolphomycin and its pharmaceutically acceptable salts are useful as antibiotics (e.g. against gram-positive pathogenic bacteria such as *Streptococcus pneumoniae, Streptococcus pyogenes, Streptococcus faecalis* and *Straphylococcus aureus*) and as antitumor agents for inhibition of mammalian malignant tumors such as leukemia L1210. The invention includes within its scope pharmaceutical compositions containing an effective antimicrobial or tumor-inhibiting amount of rudolphomycin or a pharmaceutically acceptable salt thereof in combination with an inert pharmaceutically acceptable carrier or diluent. The compositions may also contain other active antimicrobial or antitumor agents. Such compositions may be made up in any pharmaceutical form appropriate for the route of administration in question. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antimicrobial agent the compound of the present invention or a salt or pharmaceutical composition thereof is administered so that the concentration of active ingredient is greater than the minimum inhibitory concentration for the particular organism being treated. A suggested dosage for use as an antitumor agent in mamalian hosts is 2.5 to 10 mg./M$^2$ for a single injection intravenous treatment course. It will of course be appreciated that the actual dose of rudolphomycin used will be determined by the physician after consideration of such factors as age, body weight, sex, diet, route of administration, rate of excretion, condition of the patient, drug combinations, and the particular situs and disease being treated.

According to another aspect of the invention, a method is provided for therapeutically treating a mammalian host affected by an antimicrobial infection (particularly a gram-positive bacterial infection) or by a malignant tumor (e.g. a solid or ascitic-type tumor such as L1210 leukemia) which comprises administering to said host an effective antimicrobial or tumor-inhibiting dose of rudolphomycin or a pharmaceutically acceptable salt thereof.

The following examples serve to illustrate the invention without limiting it. Sephadex LH-20 is the trade name of Pharmacia Fine Chemicals, Inc. for an alkylated cross-linked dextran used in adsorption and gel filtration chromatography. Quanta/Gram LQDF is the trade name of a silica gel thin layer chromatography plate manufactured by Quantum Industries, Fairfield, New Jersey. μ PORASIL is a fully porous silica adsorbent used in liquid chromatography and manufactured by Waters Associates Inc., Milford, Massachusetts. Skellysolve B is a commercially available petroleum solvent (Skelly Oil Co.) comprising isomeric hexanes and having a boiling point of 60°–68° C. The main component of Skellysolve B is n-hexane. Unless otherwise indicated, all temperatures below are in degrees Centigrade.

EXAMPLE 1

Preparation of Bohemic Acid Complex

A. Shake-flask fermentation

The organism *Actinosporangium* sp.Strain C-36,145 (A.T.C.C. 31127) is grown on an agar slant medium consisting of 2 g. D-glucose, 20 g. oatmeal, 2 g. soy peptone and 2 g. agar made up to one liter with distilled water. After at least six days growth at 27° C., spores are transferred to a 500 ml. Erlenmeyer flask containing 100 ml. of sterile medium consisting of 30 g. D-glucose, 10 g. soybean flour, 10 g. Pharmamedia (Traders Oil Mill Co., Fort Worth, Tex.) and 3 g. CaCO$_3$ made up to one liter with distilled water. This vegetative culture is incubated at 27° C. on a Gyrotary tier shaker (Model G53, New Brunswick Scientific Co., Inc.) set at 210 rev./min. describing a circle with a 5.1 cm. diameter. After 48 hours four milliliters of culture are transferred to a 500 ml. Erlenmeyer flask containing 100 ml. of sterile production medium consisting of 50 g. glycerol, 20 g. soybean flour, 10 g. peanut meal and 10 g. CaCO$_3$ made up to one liter with distilled water. The culture is incubated at 27° C. for 144 hours on a shaker set at 230 rev./min. At this time antibiotic activity consisting of the bohemic acid complex is found in the culture filtrate and mycelium.

B. Stir-jar fermentation

Bohemic acid complex is produced in stir-jar fermentors with the use of a 48 hour old vegetative culture as described in Example 1a. Four hundred milliliters of culture is transferred to 10 liters of sterile production medium as described in Example 1 including 0.01% Hodag F1 silicone antifoam (Hodag Chemical Corp., Skokie, Ill.) contained in a 14 liter capacity stir-jar. The stir-jar is installed in a Fermentor Drive Assembly (Model FS-614, New Brunswick Scientific Co., Inc., New Brunswick, N.J.). The temperature is maintained at 27° C., the air flow rate is 6 liters/min. and the agitator is set at 300 r.p.m. Hodag F1 antifoam is fed automatically as required to control foaming. At approximately 210 hours the incubation is terminated and bohemic acid complex is found in the culture filtrate and the mycelium.

C. Tank fermentation

A tank fermentor with 37.8 liters of sterile production medium (as in Example 1a) is inoculated with 1.89 liters of vegetative culture (as prepared in Example 1a), agitated with an impeller speed of 300 r.p.m., aerated at 85 liters/min. and incubated at 27° C. for 190 hours. The bohemic acid complex is found in the culture filtrate and mycelium.

D. Tank fermentation

A tank fermentor with 3028 liters of production medium (as in Example 1a) is inoculated with 152 liters of vegetative culture (as prepared in Example 1a), agitated with an impeller speed of 155 r.p.m., aerated at 141.6 liters/min. and incubated at 27° C. for 190 hours. At this time the presence of bohemic acid complex is found in the culture filtrate and mycelium.

EXAMPLE 2

Isolation of Bohemic Acid Complex

A. Whole fermentation broth (7 liters) at its harvest pH 8.1, was stirred with about an equal volume of methyl isobutyl ketone for 20-30 min. A large amount of diatomaceous earth filter aid was then added and, after stirring thoroughly to mix this in, the mixture was filtered on a filter mat using vacuum suction. The filtrate separated into two phases of which the lower-(aqueous) was discarded. The organic phase was evaporated under vacuum to a small volume (50-100 ml.) and diluted with Skellysolve B to precipitate a dark red solid which was dried in vacuo to give 1.9 g. of bohemic acid complex.

B. Large scale isolation

Whole fermentation broth (3,000 liters) at pH 8.0-8.5 was chilled at 25° C. and agitated vigorously with 3,000 liters methyl isobutyl ketone for 30 min. at 20°-30° C. To the emulsion was added 360 kg. filter aid and the mixture was stirred vigorously for another hour. It was then allowed to settle for about 30 min. after which 2,300-2,500 liters of organic phase was decanted and chilled at 0°-10° C. An additional 800 liters methyl isobutyl ketone was agitated with the mixture for 20 min., decanted after settling 30 min., and combined with the chilled first fraction to give a total extract volume of 3,300-3,400 liters. This was polish filtered to give a final 3,100-3,200 liter methyl isobutyl ketone extract free of solids and insoluble aqueous phase. The organic extract was vacuum concentrated at 0°-10° C. to a final volume of 6 liters. This was added to 60 liters Skellysolve B with stirring at 20°-25° C. The precipitated solids were collected on a Nutsche filter, washed with 10 liters Skellysolve B and sucked dry to give 900-1,000 g. somewhat oily and dark red amorphous product. This was stirred with excess ether, filtered on a Buchner funnel, rinsed with additional ether, sucked dry and dried in vacuo to give 351 g. amorphous dark red bohemic acid complex.

EXAMPLE 3

Partial Purification of Bohemic Acid Complex

A. Small-scale Purification

Crude bohemic acid complex (10 g.) as extracted from whole broth was dissolved in 1 liter of methylene chloride and extracted twice with 1 liter portions of 0.1N aqueous acetic acid. The aqueous extracts were separated and quickly adjusted with $K_2CO_3$ to pH 7.5. The resultant mixture was extracted with methylene chloride and, after separation, the organic phase was evaporated to dryness to give 2.07 g. of material. By HPLC analysis this was largely a mixture of basic constituents, particularly marcellomycin, musettamycin and rudolphomycin. Evaporation of the original methylene chloride solution gave 3.46 g. of oily material having little or none of the basic compounds.

B. Larger-scale Purification

Crude bohemic acid complex (760 g.) in 53 liters of methylene chloride was stirred with 50 liters 0.1N acetic acid at 19°-20° C. (ambient temp.) following which 0.5 kg. diatomaceous earth was added. The mixture was filtered on a 24" precoated Nutsche filter, the mat rinsed with 4 liters of methylene chloride, and the aqueous phase (47 liters) separated and neutralized with 660 g. $NaHCO_3$ to pH 7.0. The methylene chloride phase was then re-extracted and the mixture treated as before. The rich aqueous fractions were each re-extracted as soon as they had been neutralized with 760 g. $NaHCO_3$. The two rich methylene chloride extracts were combined. The later was evaporated to an oily mass and treated with diethyl ether to give 210 g. of enriched bohemic acid complex containing about 40% marcellomycin as well as substantial amounts of musettamycin and rudolphomycin. The original spent methylene chloride fraction by HPLC analysis contained none of these components.

EXAMPLE 4

Fractionation of Bohemic Acid Complex and Separation of Fraction Containing Rudolphomycin-Marcellomycin Mixture Sephadex LH-20 soaked for 68 hours in chloroform was slurry packed into a Pharmacia SR 25/100 column (25 mm. I.D. × 100 cm. height) equipped with adjustable teflon tips at each end. The column was packed so as to be completely filled from tip to tip, an effective bed height of 90-95 cm. Bohemic acid complex (500 mg.) was dissolved in 10 ml. chloroform and applied to the column which was then allowed to develop with chloroform by downflow at a take-off rate of 1 ml./min. Eluted liquid was collected in 6 ml. cuts in a fraction collector. Samplings of even numbered tubes were diluted 80-fold with chloroform and read in a Bausch and Lomb Spectronic 20 colorimeter at 490 mμ. Four distinct bands of anthracycline pigments were noted as follows:

| Tube No. | | Wgt. upon Evaporation |
|---|---|---|
| 1–4 | | — |
| 5–11 | First Band | 66 mg. |
| 12–14 | | — |
| 15–21 | Second Band | 36 mg. |
| 22–35 | | — |
| 36–44 | Third Band | 18 mg. |
| 45 | | — |
| 46–57 | Fourth Band | 48 mg. |
| 58 | | — |

The solids obtained were chromatographed on Brinkmann 60F254 silica gel thin layer plates using an 80:20 toluene:methanol solvent system. The first band to elute was shown by thin layer chromatography to be a complex inactive mixture. The second band gave a characteristic pinkish red zone at about $R_f=0.75$. This fraction was also inactive and was found to comprise mainly η-pyrromycinone. The third fraction to elute gave a single zone with $R_f \sim 0.3$. This was determined to be musettamycin and was highly active when tested on both the L1210 and P388 mouse leukemia systems. The final band to elute gave a zone of $R_f \sim 0.3$ and comprised mainly marcellomycin but also a minor proportion of rudolphomycin. This component exhibited high activity when tested on L1210 and P388 mouse leukemia systems.

EXAMPLE 5

Large Scale Fractionation to Produce Rudolphomycin-Marcellomycin Mixture

A 6 inch (diameter) × 77 inch (height) glass column was equipped at the base with a Neva Clog (Multimetal Wire Cloth Corp., Tappan, N.Y.) filter on top of which was placed a layer of glass wool followed by a circular polyethylene frit. The latter was cut to a diameter of 5⅞ inches to allow for swelling in chloroform. Sephadex LH-20 (8.73 kg.) was stirred for 3 hours in chloroform, filtered, and the solid reslurried in chloroform and left to stand for 16 hours. The mixture was then agitated for 15 min. and loaded onto the column. A 30 g. sample of bohemic acid complex (prepared as in Example 2B) was heated with 1.5 liters of chloroform for 15 min. and then stirred for 16 hours. Upon filtration, 7.5 g. of undissolved material containing some activity was separated. (In later runs it was found that the sample could be completely dissolved in chloroform containing 30–40% methanol. Chromatographic results were the same with this procedure). The filtrate was applied to the column and downward development begun with chloroform. A flow rate of 16 ml./min. at takeoff was maintained throughout the run. An initial volume of 1,445 ml. of eluant was taken before color reached the bottom of the gel bed. At this point collection of 100 ml. fractions was initiated and continued until the liquor was quite light again, a total of 906 cuts. Aliquots of every fifth fraction were diluted and analyzed as described in Example 4. Four components were seen to have separated as indicated below.

| Fraction | Description | Wgt. upon Evaporation |
|---|---|---|
| 1–20 | 1st component, mixture*, inactive | 6.74 g. |
| 21–44 | 2nd component, mixture, inactive** | 4.18 g. |
| 45–53 | trough - discarded | 385 mg. |
| 54–70 | 3rd component, single compound-musettamycin, active | 1.45 g. |
| 71–75 | trough - discarded | 198 mg. |
| 76–110 | 4th component, mixture comprising mainly marcellomycin but also minor amount of rudolphmycin, active | 4.03 g. |
| 111–200 | post cut | 1.72 g. |

*as evidenced by thin layer chromatography
**mainly η-pyrromycinone

EXAMPLE 6

Separation and Isolation of Rudolphomycin from Rudolphomycin Marcellomycin Mixture Silica gel (Grace Davison, grade 62) was acid washed with 6N HCl at 100° C., rinsed until neutral with deionized water and air dried overnight at 110°. Of the adsorbant so obtained, 770 g. was slurried in 8:2 (v/v) toluene:methanol. Concentrated ammonium hydroxide was then added dropwise to the stirred mixture until a pH of 8 was obtained. About 12 ml. concentrated NH₄OH was required. The neutralized silica gel was then slurry packed in a Fisher-Porter glass column, 50 mm. diameter × 120 cm. height using a column extender in order to completely fill the column. When the bed was well settled, the extender was removed with excess silica leaving an effective bed height of 119 cm. The column was then capped and equipped with input tubing from a solvent reservoir.

A sample of solids obtained by evaporation of the fourth peak material from Sephadex LH-20 chromatography of bohemic acid complex (see Examples 4 and 5), 1.02 g., was stirred in about 30 ml. of 19:1 toluene:methanol (v/v). Addition of about 3 ml. additional methanol resulted in complete dissolution of the solids, the solution then being applied carefully to the top of the column. Development of the column was begun with 19:1 toluene:methanol (v/v) at a 0.9 ml./min. flow rate. Eluate was sent to waste until the color front had nearly reached the bottom of the column at which point collection of 20 ml. fractions was begun. Portions (20 ul.) of each fraction were spotted on Quanta/Gram LQDF thin layer chromatography plates and the latter developed in a 6:2:2 toluene:methanol:acetone (v/v) system. Cuts were made by pooling fractions according to the components detected by thin layer chromatography and these were evaporated to dryness. Results are indicated below. Fractions 21–120 having an $R_f$ of 0.32 were essentially pure rudolphomycin.

| Cut No. | Fractions No. | Wgt. | $R_f$ | Constituent |
|---|---|---|---|---|
| 1 | Foreshot[1] | 160 mg. | 0.76 | η-pyrromycinone |
| 2 | 1–20 | 7 mg. | 0.76 | η-pyrromycinone |
| 3 | 21–120 | 161 mg. | 0.32 | rudolphomycin |
| 4 | 121–160 | 19 mg. | 0.32, 0.29 | mixture[2] |
| 5 | 161–238 | 278 mg. | 0.29 | marcellomycin |

[1] slight color was seen in 4 l. prior to cut 2
[2] rudolphomycin and marcellomycin The column was then stripped with pure methanol to afford an additional 240 mg. of pigmented mixture of low biological activity.

EXAMPLE 7

Fractionation of Marcellomycin-Rudolphomycin Mixture on a Large Scale

Silica gel was prepared and equilibrated with 19:1 toluene:methanol (v/v) as described in Example 6, using about 7.5 kg. silica. This was packed into a glass column having a 6 inch diameter. A sample of fourth peak material (from Sephadex LH-20 chromatography of bohemic acid complex), 10 g., dissolved in the solvent system as described in Example 6, was applied evenly at the top of the bed and drawn down onto the latter. Development with 19:1 toluene:methanol (v/v) was then begun. In this case the silica appeared more active as elution was considerably slower. Therefore, after three days the methanol content was increased by 1% (from 5% initially) each day to 10%.

Fractions of 200 ml. each were collected and determined according to visible adsorption at 490 nm using a Brinkmann PC/600 probe colorimeter with the probe set for the shortest usable pathlength. There was relatively little color in the first 240 fractions. In later fractions a precipitate often formed upon concentration and this was collected separately. Results are tabulated below. Substantially pure rudolphomycin was found in cut 3 (fractions 258–283).

and $\eta$-pyrromycinone) and four fractions were collected as follows:

| Cut No. | Wgt. | $R_f$* | constituents |
|---|---|---|---|
| Forecut | — | — | $\eta$-pyrromycinone |
| 1 | 244 mg. | 0.34 | rudolphomycin |
| 2 | 110 mg. | 0.34 | rudolphomycin |
| 3 | 190 mg. | 0.34 | rudolphomycin |
| 4 | 310 mg. | 0.34 | rudolphomycin |

*Solvent system toluene-methanol:acetone (3:1:1) (v/v) on precoated TLC silica gel plates (60F-254)

The above rudolfomycin fractions were shown by TLC and PMR spectroscopy to be identical and to be substantially pure rudolphomycin.

EXAMPLE 9

HPLC Separation of Marcellomycin-Rudolphomycin Mixture

A. Analytical HPLC System

A mixture of 960 ml. methylene chloride*, 40 ml. methanol* and 10 ml. concentrated aqueous NH$_4$OH was stirred for 5–10 minutes, placed under water pump vacuum with stirring for about 30 seconds to degas (this step is probably not critical as methylene chloride systems do not appear to have any appreciable dissolved

| Cut No. | Fraction No. | Wgt. | | State[1] | $R_f$[2][6] | Constituent(s) |
|---|---|---|---|---|---|---|
| Foreshot | — | 104 | mg. | crystn. ppt.[3] | 0.7, tailing | $\eta$-pyrromycinone[4] |
| 1 | 1–240 | 545 | mg. | crystn. ppt. | 0.7, tailing | $\eta$-pyrromycinone[4] |
| 1 | 1–240 | 150 | mg. | amorph. | (0.31), (0.51), (0.53), 0.7 | mixture[4] |
| 2 | 241–257 | 108 | mg. | amorph. | (0.31), 0.7 | mixture[4] |
| 3 | 258–283 | 352 | mg. | crystn. ppt. | (0.31), 0.7 | rudolphomycin[4] |
| 3 | 258–283 | 218.5 | mg. | crystn. | (0.27), 0.31, 0.7 | rudolphomycin[4] |
| 4 | 284–314 | 929 | mg. | amorph. | (0.27), 0.31, (0.7) | rudolphomycin[4] |
| 5 | 315–339 | 663 | mg. | amorph. ppt. | 0.27, 0.31 | rudolphomycin and marcellomycin |
| 5 | 315–339 | 1125 | mg. | amorph. | 0.27, (0.31) | rudolphomycin and marcellomycin |
| 6 | 340–365 | 1330 | mg. | amorph. ppt. | 0.27, (0.31) | marcellomycin |
| 6 | 340–365 | 237 | mg. | amorph. | 0.27, (0.31) | marcellomycin |
| 7 | 366–440 | 1512 | mg. | amorph. ppt. | 0.27, (0.31) | marcellomycin |
| 7 | 366–440 | 192 | mg. | amorph. | 0.27, (0.31) | marcellomycin |
| postcut | 366–440 | 1735 | mg. | amorph. ppt. | 0.12–0.26[5] | unknown |
| postcut | | 1600 | mg. | amorph. | 0.12–0.26[5] | unknown |

[1]Precipitates (ppt.) listed were components which came out of solution during concentration and were collected by filtration. Other materials tabulated were obtained by evaporation of the liquid or mother liquor to dryness or near dryness and dilution with Skellysolve B to precipitate a solid.
[2]$R_f$ values in parenthesis are for weak or very weak zones.
[3]Evaporation of the mother liquor from this fraction gave too little material to evaluate.
[4]$\eta$-Pyrromycinone appears in the foreshot and first 4 cuts in increasingly smaller amounts. Except for the foreshot and cut 1 there is relatively little of it in these.
[5]The postcut solids showed a smearing of zones by TLC.
[6]$R_f$ values determined by silica gel thin layer chromatography with (6:2:2) toluene:methanol:acetone (v/v) system
$R_f = 0.7$ - $\eta$-pyrromycinone
$= 0.31$ - rudolphomycin
$= 0.27$ - marcellomycin.

EXAMPLE 8

Purification of Rudolphomycin

A single column of silica gel (Waters Associates Prep PAK-500/silica) was equilibrated with a solvent mixture consisting of 12% methanol in methylene chloride on the Waters Associates Prep LC/500 high pressure liquid chromatography instrument. Fractions containing primarily rudolphomycin from the large scale silica gel chromatography of the rudolphomycin-marcellomycin mixture (Example 7) were combined and 1.16 g. of such material was chromatographed in two portions. The sample was dissolved in about 10 ml. of the solvent mixture following which it was injected onto the column. The column was developed at a flow rate of 500 ml./min. following a fore-cut (primarily solvent front air) and then allowed to stand until the mixture became clear (at this point an aqueous puddle is found floating on top).

*Solvents were filtered through a 10 $\mu$m pore size Millipore (Trademark of Millipore Corp., Bedford, Mass.) filter to remove any particulate matter.

The HPLC apparatus used in this procedure consisted of a Waters Model M-6000A Solvent Delivery System, a Model U6K injector with 2 ml. loop, a $\mu$-porasil prepacked column (analytical column 1/4 in. ID (internal diameter) by 30 cm. length containing highly purified silica, 10$\mu$ particle size, surface area 400 M$^2$/g, available from Waters Associates) and a Varian Model 635 M variable wavelength (UV and visible) spectrophotometer with a microvolume cell flow assembly (Variscan LC Detector, available from Varian Instrument Division, Palo Alto, Calif.). Solvent feed to the pump was made via Teflon tubing equipped at the inlet end with a stainless steel depth filter. Components were connected by 0.23 mm ID stainless steel tubing using minimal distance.

The lower major phase of the solvent prepared above was pumped through the column to pre-equilibrate it, using a volume roughly equivalent to 40 column volumes (about 160 ml.). Samples of 1–20 μg. were generally applied depending on the number of components expected. In following preparative runs it was often necessary to concentrate samples in order to inject enough material.

Because of the water and ammonia present in the solvent system, the column would gradually lose activity. Therefore, it was necessary to run standards from time to time. When retention times became low enough to begin to endanger resolution, the column was regenerated according to procedures recommended by the manufacturer. Following this and re-equilibration with the solvent system, the column was invariably found to be restored to its initial activity in that system.

Use of the above analytical HPLC system resolved the components of bohemic acid complex nicely. The relative positions of marcellomycin, musettamycin and rudolphomycin were determined by running the pure compounds.

B. Preparative HPLC System

The column chamber of a Waters Prep LC/System 500 apparatus (Waters Associates, Inc., Milford, Mass.) was loaded with one Prep PAK-500 Silica column and placed under a radial pressure of 30 atm. The column was then equilibrated with the lower phase of a solvent system consisting of methylene chloride:methanol:concentrated aqueous ammonium hydroxide 95.5:4.5:0.5 (v/v), prepared the day before and allowed to stand overnight, passing several liters through to waste and then recirculating back to the solvent reservoir for 30–60 min. Often, when a new Prep PAK was being used for the first time, preequilibration with methylene chloride containing 10–20% methanol and 2–5% concentrated aqueous ammonium hydroxide was carried out, pumping most of a 5 l. batch of the mixture through the column and recirculating the last portion for about 20 min.

A sample of the rudolphomycin-marcellomycin mixture, 3 g., from Sephadex LH-20 chromatography (Example 5) was dissolved in 30 ml. of the above-mentioned solvent system and filtered. The solution was pumped onto the column via one of the solvent inlet ports, following which elution was begun from the main solvent reservoir through the other inlet. A flow rate was maintained at 250 ml./min. The effluent stream was monitored by the built-in RI (reflective index) detector which monitors 1–2% of the stream diverted via a stream splitter. A chart speed of 2 mm./cm. and sensitivity setting of 20 were maintained.

The RI detector showed two distinct peaks which were collected in fractions more or less arbitrarily. These were evaluated by analytical HPLC which showed the first peak (fractions 4–12) to be rudolphomycin (>98% pure) and the second marcellomycin. Because of tailing the marcellomycin fractions were contaminated with small amounts of rudolphomycin, particularly the earlier ones. Therefore fractions 13–19, 13 being about a 1:1 mixture and the rest being mostly marcelloycin, were combined and pumped back through the Prep LC/500 apparatus without any prior concentration. Again two peaks were seen on the RI detector, here closer together than in the first pass. However the first yielded on work-up a small additional amount, 35 mg., of rudolphomycin and the second gave marcellomycin, 711 mg., virtually free of rudolphomycin. Only 81 mg. of mixture was obtained from the intermediate fraction between the peaks.

From the first pass 1.036 g. of rudolphomycin and 791 mg. marcellomycin were obtained. Overall, combining the appropriate fractions from the second pass with these, yields of 1.07 g. rudolphomycin (35.7%) and 1.50 g. marcellomycin (50%) were realized.

We claim:

1. The anthracycline antibiotic, rudolphomycin, or a pharmaceutically acceptable salt thereof, said antibiotic being substantially free of substances co-produced therewith and having the structural formula:

* * * * *